(12) United States Patent
Matsuzaki et al.

(10) Patent No.: US 6,585,986 B2
(45) Date of Patent: Jul. 1, 2003

(54) GELLING AGENT AND GEL COMPOSITIONS

(75) Inventors: Fumiaki Matsuzaki, Yokohama (JP); Toshio Yanaki, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 90 days.

(21) Appl. No.: 09/759,342

(22) Filed: Jan. 16, 2001

(65) Prior Publication Data

US 2001/0044475 A1 Nov. 22, 2001

Related U.S. Application Data

(63) Continuation-in-part of application No. 09/147,536, filed as application No. PCT/JP98/02369 on May 28, 1998, now abandoned.

(30) Foreign Application Priority Data

May 30, 1997 (JP) .............................................. 9-157809

(51) Int. Cl.$^7$ .......................... A61K 7/00; A61K 33/06; A61K 47/00
(52) U.S. Cl. ........................ 424/401; 424/684; 574/770
(58) Field of Search ................................ 424/401, 684; 514/770

(56) References Cited

FOREIGN PATENT DOCUMENTS

JP          62020179        *   2/1987

* cited by examiner

*Primary Examiner*—Shelley A. Dodson
(74) *Attorney, Agent, or Firm*—Townsend & Banta

(57) ABSTRACT

A gelation agent or an emulsifying agent is provided which is obtained by mixing a water swelling clay mineral with a quarternary ammonium salt type cation surfactant and a fatty acid or a higher alcohol which is liquid at normal temperatures. The present invention can provide a gelation agent or an emulsifying agent which can be added and mixed to a wide range of oils to produce a gel composition or an emulsified composition with superior stability, safety and usability.

The gelation agent or the emulsifying agent of the present invention or the gel composition or the emulsified composition using this agent is preferably used as the base agent of cosmetics and quasi-drugs, for example.

Also, the sunscreen cosmetic prepared by adding ultraviolet light protection powder to the aforementioned emulsified composition exhibits superior usability, i.e. it exhibits good adhesion to the skin and superior water resistance and it does not become conspicuous when the applied site comes in contact with sweat or water from the ocean or pool. Therefore, it is particularly useful when a high ultraviolet light protection effect is desired because it allows the required amount of the ultraviolet light protection powder to be blended in without concern for conspicuous whiteness.

11 Claims, No Drawings

GELLING AGENT AND GEL COMPOSITIONS

This is a Continuation-In-Part application of application Ser. No. 09/147,536 filed Jan. 19, 1999, now abandoned which is a 371 of PCT/JP98/06369, filed May 28, 1998.

FIELD OF THE INVENTION

The present invention relates to a gelation agent and a gel composition. More specifically, the present invention relates to a gelation agent which can be added and mixed to a wide range of oils to produce oil based gels with superior stability, safety and usability for applications such as cosmetics and quasi-drugs, as well as a gel composition.

The present invention relates to an emulsifying agent and an emulsified composition. More specifically, the present invention relates to an emulsifying agent which can be added and mixed to a wide range of oils to achieve the water-in-oil type (hereafter referred to as the W/o type) emulsion without using a conventional nonionic surfactant, and an emulsified composition with superior stability, safety and usability using this emulsifying agent.

The present invention relates to a sunscreen cosmetic. More specifically, the present invention relates to a sunscreen cosmetic which has the characteristics of having superior water resistance as well as preventing the whiteness of the ultraviolet light protection powder from being conspicuous.

BACKGROUND OF THE INVENTION

Conventionally, for oil swelling gelation agents, it has been known that a gel with good usability can be prepared by mixing a specific nonionic surfactant with an organic modified clay mineral obtained by exchanging water and/or exchangeable cations in between layers of a water swelling clay mineral (hereafter referred to as a clay mineral) with quaternary ammonium salt type organic cations by means of the cation exchange. Another known gelation method uses a gelation agent obtained by treating the organic modified clay mineral with a compound lipid instead of the nonionic surfactant.

However, a gelation method using the aforementioned gelation agent requires that the nonionic surfactant and the compound lipid have to be selected for each oil component to be used to obtain gel with good stability and usability because the structure of the obtained gel is significantly different depending on the oil component used.

Also, gels which can maintain sufficient stability tend to spread poorly at the time of application and exhibit poor usability.

Based on the aforementioned problem, the inventors conducted earnest research and discovered that a gelation agent obtained by mixing a water swelling clay mineral with a quaternary ammonium salt type cation surfactant and a fatty acid which is liquid at normal temperatures can provide an oil based gel with superior stability, safety and usability when used with a wide range of oil components, thus completing the present invention.

Furthermore, the inventors discovered that a gelation agent obtained by mixing a water swelling clay mineral with a quaternary ammonium salt type cation surfactant and a higher alcohol which is liquid at normal temperatures can provide an oil based gel with superior stability, safety and usability when used with a wide range of oil components, thus completing the present invention.

The object of the present invention is to provide a gelation agent which can be added and mixed to a wide range of oils to produce an oil based gel with superior stability, safety and usability, as well as a gel composition which uses this gelation agent.

Conventionally, a lipophilic surfactant with a HLB value of 1–12, e.g. polyhydric alcohol fatty acid ester type surfactants such as glycerine fatty acid esters and sorbitan fatty acid esters have been used for the emulsifying agent to obtain a W/O type emulsified composition.

Examples of emulsifying agents which can stably emulsify a wide range of oils include an emulsifying agent composition comprising an organic modified clay mineral and a nonionic surfactant as disclosed in Japanese unexamined patent publication Tokkai Sho 61-129033, and examples of emulsifying agent compositions which can stably emulsify silicon oil, which is hard to emulsify, include a combination of an organic modified clay mineral and a polyoxyalkylene modified organo polysiloxane as disclosed in Tokkai Sho 61-212321.

However, with the aforementioned emulsifying agents, the type of the emulsifying agent has to be selected according to each oil to be used in order to obtain an emulsified composition with good stability and usability.

Also, a large quantity of the emulsifying agent is required to emulsify a large quantity of polar oil and the use of a large quantity of the emulsifying agent sometimes affects the stability and usability of the emulsified composition.

Based on the aforementioned problem, the inventors conducted earnest research and discovered that an emulsifying agent obtained by mixing a water swelling clay mineral with a quaternary ammonium salt type cation surfactant and a fatty acid which is liquid at normal temperatures can provide an emulsified composition with superior stability, safety and usability when used with a wide range of oil components, thus completing the present invention.

Also, the inventors conducted earnest research and discovered that an emulsifying agent obtained by mixing a water swelling clay mineral with a quaternary ammonium salt type cation surfactant and a higher alcohol which is liquid at normal temperatures can provide an emulsified composition with superior stability, safety and usability when used with a wide range of oil components, thus completing the present invention.

The object of the present invention is to provide an emulsifying agent which can be added and mixed to a wide range of oils to produce a W/O type emulsified composition with superior stability, safety and usability, as well as a W/O type emulsified composition which uses this emulsifying agent.

A water-in-oil type emulsified composition (hereafter also referred to as a W/O type emulsified composition) has been used in sunscreen cosmetics because it makes a base agent with superior water resistance.

In general, a W/O type emulsified composition has a shortcoming in that a system with superior temperature stability and usability is difficult to obtain. An example of the technology which addresses this shortcoming is a W/O type emulsified composition obtained by treating a water swelling clay mineral with a quaternary ammonium salt type cation surfactant and a nonionic surfactant (Tokkai Sho 61-114721, Tokkai Sho 61-129033 and Tokkai Sho 61-212321).

Also known are a sunscreen cosmetic which is prepared by adding titanium oxide and/or zinc oxide, as the ultraviolet light protection agent, to a W/O type emulsified composition made with this technology, as well as technology which uses water repellent spindle-shaped titanium oxide to make the color of the ultraviolet light protection powder less conspicuous when applied (Tokkai Hei 7-258055).

However, the conventional sunscreen cosmetics which contain ultraviolet light protection powder have a problem in that the ultraviolet light protection powder becomes conspicuously white upon contact with sweat or water from the ocean or pool.

Shiseido Co., Ltd. application No. 62-30179 (hereinafter '179), published Feb. 9, 1987, discloses gelation agents for cosmetics prepared by treating swellable clay minerals with quaternary ammonium salt-type cationic surfactants and complex lipids. However, the '179 reference does not contain either a fatty acid which is liquid at normal temperature or a higher alcohol which is liquid at normal temperature, as in the gellation agent of the present invention. These two elements provide desired characteristics, and constitute important aspects of the present invention.

Based on the aforementioned problem, the inventors conducted earnest research to obtain a W/O type emulsified composition using the aforementioned organic modified clay mineral which does not become conspicuously white upon contact with water. The inventors discovered that this problem can be solved by using fatty acids or higher alcohols which are liquid at normal temperatures instead of the conventional nonionic surfactants, thus completing the present invention.

The object of the present invention is to provide a sunscreen cosmetic which has the characteristics of having superior water resistance and keeping the whiteness of the ultraviolet light protection powder less conspicuous upon contact with water.

SUMMARY OF THE INVENTION

The present invention provides a gelation agent which is characteristically obtained by mixing a water swelling clay mineral with a quaternary ammonium salt type cation surfactant and a fatty acid which is liquid at normal temperatures.

Also, the present invention provides said gelation agent wherein the blend ratio of said quaternary ammonium salt type cation surfactant is 60–140 mili-equivalents for 100 g of said water swelling clay mineral.

Furthermore, the present invention provides said gelation agent wherein the blend ratio of said fatty acid which is liquid at normal temperatures is 1–500 g for 100 g of said water swelling clay mineral.

Also, the present invention provides a gel composition which contains said gelation agent and an oil component.

Furthermore, the present invention provides a gelation agent which is obtained by mixing a water swelling clay mineral with a quaternary ammonium salt type cation surfactant and a higher alcohol which is liquid at normal temperatures.

Also, the present invention provides said gelation agent wherein the blend ratio of said quaternary ammonium salt type cation surfactant is 60–140 mili-equivalents for 100 g of said water swelling clay mineral.

Furthermore, the present invention provides said gelation agent wherein the blend ratio of said higher alcohol which is liquid at normal temperatures is 1–500 g for 100 g of said water swelling clay mineral.

Also, the present invention provides a gel composition which contains said gelation agent and an oil component.

Further, the present invention provides an emulsifying agent which is obtained by mixing a water swelling clay mineral with a quaternary ammonium salt type cation surfactant and a fatty acid which is liquid at normal temperatures.

Also, the present invention provides said emulsifying agent wherein the blend ratio of said quaternary ammonium salt type cation surfactant is 60–140 mili-equivalents for 100 g of said water swelling clay mineral.

Furthermore, the present invention provides said emulsifying agent wherein the blend ratio of said fatty acid which is liquid at normal temperatures is 1–500 g for 100 g of said water swelling clay mineral.

Also, the present invention provides an emulsified composition which contains said emulsifying agent, an oil component and water.

Furthermore, the present invention provides an emulsifying agent which is obtained by mixing a water swelling clay mineral with a quaternary ammonium salt type cation surfactant and a higher alcohol which is liquid at normal temperatures.

Also, the present invention provides said emulsifying agent wherein the blend ratio of said quaternary ammonium salt type cation surfactant is 60–140 mili-equivalents for 100 g of said water swelling clay mineral.

Furthermore, the present invention provides said emulsifying agent wherein the blend ratio of said higher alcohol which is liquid at normal temperatures is 1–500 g for 100 g of said water swelling clay mineral.

Also, the present invention provides a gel composition which contains said emulsifying agent, an oil component and water.

The present invention provides a sunscreen cosmetic wherein said emulsified composition additionally contains ultraviolet light protection powder.

BEST MODES OF THE EMBODIMENTS

The components of the present invention are described in detail below.

"Gelation agent, gel composition, emulsifying agent, emulsified composition"

The water swelling clay mineral used in the present invention is a type of colloidal hydrated aluminum silicate with a three-layer structure represented by the following general formula.

$$(X, Y)_{2-3}(Si, Al)_4O_{10}(OH)_2Z_{1/3} \cdot nH_2O$$

Where,
X: Al, Fe(III), Mn(III), Cr(III),
Y: Mg, Fe(II), Ni, Zn, Li, Mn(II), and
Z: K, Na, ½ Ca, ½ Mg.

Specific examples include natural or synthetic (in this case this refers to those whose (OH) groups in the formula are replaced by fluorine) montmorillonites including montmorillonite, saponite and hectorite (commercially available examples include beagum, kunipia and laponite) and synthetic mica known under names such as sodium silicic mica and sodium or lithium teniorite (commercially available examples include Daimonait from Topi Kogyo).

The quaternary ammonium salt type cation surfactant used in the present invention is represented by the following general formula:

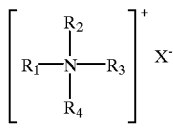

(In this formula, $R_1$ denotes a benzyl group or alkyl group with a carbon number of 10–22, $R_2$ denotes a methyl group or alkyl group with a carbon number of 10–22, $R_3$ and $R_4$ are hydroalkyl groups or alkyl groups with a carbon number of 1–3, and X denotes a halogen atom or methyl sulfate residue.)

Specific examples include dodecyltrimethylammonium chloride, myristyltrimethylammonium chloride, cetyltrimethylammonium chloride, stearyltrimethylammonium chloride, arachiltrimethylammonium chloride, behenyltrimethylammonium chloride, myristyldimethylethylammoium chloride, cetyldimethylethylammoium chloride, stearyldimethylethylammoium chloride, arachildimethylethylammoium chloride, behenyldimethylethylammoium chloride, myristyldiethylmethylammonium chloride, cetyldiethylmethylammonium chloride, stearyldiethylmethylammonium chloride, arachilidiethylmethylammonium chloride, behenyldiethylmethylammonium chloride, benzyldiethylmethylammonium chloride, benzyldimethylcetylammonium chloride, benzyldimethylstearylammonium chloride, benzylmethylbehenylammonium chloride, benzylmethylethylcetylammonium chloride, benzylmethylethylstearylammonium chloride, and dibehenylhydroxyethylammonium chloride, as well as the corresponding bromide and such, and dipalmitylpropylammonium methylsulfate. When implementing the present invention, one or more types among these are selected at will.

Examples of the fatty acid which is liquid at normal temperatures for use in the present invention include oleic acid, isostearic acid, linoleic acid, linolenic acid, eicosapentaenoic acid and docosahexaenoic acid. When implementing the present invention, one or more types among these are selected at will.

Examples of the higher alcohol which is liquid at normal temperatures for use in the present invention include oleyl alcohol, isostearyl alcohol, octyldodecanol, decyltetradecanol and jojoba alcohol. When implementing the present invention, one or more types among these are selected at will.

The gelation agent or the emulsifying agent of the present invention can be prepared by simply mixing the aforementioned essential ingredients. For example, the preparation can be done by dispersing/stirring a clay mineral, quarternary ammonium salt type cation surfactant, and a fatty acid or higher alcohol which is liquid at normal temperatures in a solvent with a low boiling point, such as water, acetone, or lower alcohols, or by pretreating the clay mineral and quarternary ammonium salt type cation surfactant in the solvent with a low boiling point to obtain the cation modified clay mineral (hereafter also referred to as an organic modified clay mineral) and mixing it with a fatty acid or higher alcohol which is liquid at normal temperatures, followed by removal of the solvent with a low boiling point. In the present invention, it is also possible to use the product without removing the solvent with a low boiling point.

When the quaternary ammonium salt type cation surfactant and the fatty acid or higher alcohol which is liquid at normal temperatures enter between the layers of the clay mineral, the interlayer space of the clay mineral becomes expanded. Therefore, adsorption of the quarternary ammonium salt type cation surfactant and the fatty acid or higher alcohol which is liquid at normal temperatures can be verified by measuring the basal spacing with the X-ray diffraction method.

In the gelation agent or the emulsifying agent of the present invention, the content of the quarternary ammonium salt type cation surfactant is preferably 60–140 miliequivalents for 100 g of the clay mineral. In the gelation agent or the emulsifying agent of the present invention, the content of the fatty acid or higher alcohol which is liquid at normal temperatures is preferably 1–500 g, more preferably 5–400 g, for 100 g of the clay mineral. If the content of the fatty acid or higher alcohol is less than 1 g, then the interlayer spacing of the clay mineral does not expand and the gelation capability becomes insufficient. If it is more than 500 g, then the stability of the gel over time may become poor.

The gelation agent of the present invention can be added to a wide range of oils to produce an oil based gel with superior stability, safety, and usability compared with conventional gelation agents which use clay minerals.

The emulsifying agent of the present invention can be added to a wide range of oils and water to obtain a W/O type emulsified composition with superior stability, safety, and usability compared with conventional gelation agents which use clay minerals.

For the oil component used in the gel composition or the emulsified composition of the present invention, all the common oil components used in cosmetics, drugs, etc., ranging widely from polar oils to nonpolar oils, can be used.

Specific examples of the liquid oil component used in the present invention include avocado oil, tsubaki oil, turtle oil, macadamia nut oil, corn oil, mink oil, olive oil, rape seed oil, egg Yolk oil, sesame seed oil, persic oil, wheat germ oil, sasanqua oil, castor oil, linseed oil, safflower oil, cotton seed oil, perilla oil, soy bean oil, peanut oil, tea seed oil, kaya oil, rice bran oil, chinese wood oil, Japanese wood oil, jojoba oil, germ oil, triglycerol, glyceryl trioctanoate and glyceryl triisopalmitate.

Examples of the solid oil/fat include cacao butter, coconut oil, horse tallow, hardened coconut oil, palm oil, beef tallow, sheep tallow, hardened beef tallow, palm kernel oil, pork tallow, beef bone tallow, Japanese core wax, hardened oil, neatsfoot tallow, Japanese wax and hydrogenated castor oil.

Example of the wax include honeybee wax, candelilla wax, cotton wax, carnauba wax, bayberry wax, tree wax, whale wax, montan wax, bran wax, lanolin, kapok wax, lanolin acetate, liquid lanolin, sugar cane wax, lanolin fatty acid isopropyl ester, hexyl laurate, reduced lanolin, jojoba wax, hard lanolin, shellac wax, POE lanolin alcohol ether, POE lanolin alcohol acetate, POE cholesterol ether, lanolin fatty acid polyethylene glycol and POE hydrogenated lanolin alcohol ether.

Examples of the hydrocarbon oil include liquid paraffin, ozokerite, squalene, pristane, paraffin, ceresin, squalene, vaseline and microcrystalline wax.

Examples of the higher fatty acid include lauric acid, myristic acid, palmitic acid, stearic acid, behenic acid, oleic acid, 12-hydroxystearic acid, undecylenic acid, and tall oil.

Examples of the higher alcohols include cetyl alcohol, stearyl alcohol, behenyl alcohol, myristyl alcohol, and cetostearyl alcohol.

Examples of the synthetic ester oil include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexylate, dipentaerythritol fatty acid ester, N-alkyl glycol monoisostearate, neopentyl glycol dicaprylate, diisostearyl malate, glyceryl di-2-heptylundecanoate, trimethylolpropane tri-2-ethylhexylate, trimethylolpropane triisostearate, pentane erythritol tetra-2-ethylhexylate, glyceryl tri-2-ethylhexylate, trimethylolpropane triisostearate, cetyl 2-ethylhexanoate, 2-ethylhexyl palmitate, glyceryl trimyristate, glyceride tri-2-heptylundecanoate, methyl castor oil fatty acid, oleyl oleate, cetostearyl alcohol, aceto glyceride, 2-heptylundecyl palmitate, diisobutyl adipate, 2-octyldodecyl N-lauroyl-L-glutamate, di-2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate.

Examples of the silicone oil include chain polysiloxanes including dimethylpolysiloxane, methylphenylpolysiloxane, and methylhydrogenpolysiloxane, as well as ring polysiloxanes including decamethylpolysiloxane, dodecamethylpolysiloxane and tetramethyltetrahydrogenpolysiloxane. In the present invention, one or more types among these are selected at will.

The blend ratio of the oil component in the total gel composition of the present invention is 20–95 wt %, preferably 30–80 wt %. If the blend ratio is 20 wt % or less, then an oil based composition with good usability cannot be obtained. If it is more than 95 wt % then the stability over time may deteriorate.

The blend ratio of the oil component in the total emulsified composition of the present invention is not limited, but the preferable range is 20–80 wt % of the total emulsified composition. The blend ratio of water is not limited, but the preferable range is 20–80 wt % of the total emulsified composition. The blend ratio of the aforementioned emulsifying agent required to emulsify the oil component and water is determined based on the blend ratios of the oil component and water such that a stable emulsified composition can be obtained.

Other ingredients normally blended into cosmetics, such as antioxidants, humectants, ultraviolet light absorbents, preservatives, perfumes and drugs, can be blended in the gel composition or the emulsified composition of the present invention as necessary within the range which does not affect the object of the present invention.

The gel composition or the emulsified composition of the present invention can be prepared by directly mixing the gelation agent or the emulsifying agent of the present invention and the oil component (and water) or a composition containing the oil component (and water). The mixing can be conducted using a weak mixing power method such as hand stirring, but it is more preferable to use a mixing device such as a disper, homogenizer, roller, TK mill, hoovermarler, kneader or ball mill. For directly obtaining the target oil based gel composition or emulsified composition such as a cosmetic or quasi-drug without doing the dilution, it is preferable to use a mixing device such as a disper or homogenizer. For obtaining a storable highly viscous oil based gel composition or emulsified composition so that the target oil based gel composition or emulsified composition can be obtained by diluting it as necessary, it is preferable to use a mixing device with strong mixing power such as a roller.

When preparing the gel composition or the emulsified composition, the ingredients of the gelation agent or the emulsifying agent, i.e. the water swelling clay mineral, the quarternary ammonium salt type cation surfactant, and fatty acid or higher alcohol which is liquid at normal temperatures, can be either separately added to and mixed with the composition containing the oil component (and water) or mixed together with the oil component (and water) and other ingredients. It is also possible to prepare the organic modified clay mineral by mixing the water swelling clay mineral and the quarternary ammonium salt type cation surfactant in advance and then add and mix this and the fatty acid or higher alcohol which is liquid at normal temperatures into the composition containing the oil component (and water) or mix them together with the oil component (and water) and other ingredients.

The gel composition or the emulsified composition which uses the gelation agent or the emulsifying agent of the present invention has superior stability and usability and therefore is preferably used in applications such as cosmetics and quasi-drugs.

"Sunscreen cosmetic"

The sunscreen of the present invention, i.e. said emulsified composition additionally containing ultraviolet light protection powder, has the characteristics of having superior water resistance and preventing the whiteness of the ultraviolet light protection powder from being conspicuous.

Examples of the ultraviolet light protection powder used in the present invention include titanium oxide, fine particle titanium oxide, zinc oxide, fine particle zinc oxide, iron oxide, and fine particle iron oxide. If necessary, these ultraviolet light protection powders can also be dispersed in the oil component as hydrophobic powder by means of a surface treatment such as the oil treatment method in which fat/oil is adsorbed to the surface or esterization or etherization using functional groups such as hydroxyl groups is used, the metal soap treatment method in which a zinc salt and/or a magnesium salt of a fatty acid is used, the silicone treatment method in which dimethyl polysiloxane or methyl hydrogen polysiloxane is used, and the fluorine treatment method which uses a fluorine compound containing perfluoroalkyl groups.

The blend ratio of the ultraviolet light protection powder in the sunscreen cosmetic is normally 1–50 wt %. If it is less than 1 wt %, then the ultraviolet light protection effect is low, and if it is more than 50 wt %, then aggregation of the powder and such occur, which may lead to poor usability.

The sunscreen cosmetic of the present invention can be obtained by preparing in advance the organic modified clay mineral, i.e. the emulsifying agent, by treating a water swelling clay mineral with a quarternary ammonium salt type cation surfactant and a fatty acid or higher alcohol which is liquid at normal temperatures, and then emulsifying the oil phase prepared by mixing the oil component and the water phase in which a hydrophilic ultraviolet light protection powder is dispersed with a conventional method. When using a lipophilic ultraviolet light protection powder, it is preferable to disperse the powder in the oil phase.

It is also possible to carry out the emulsification without preparing the emulsifying agent in advance, i.e. the water swelling clay mineral, the quarternary ammonium salt type cation surfactant, the fatty acid or higher alcohol which is liquid at normal temperatures and the ultraviolet light protection powder can be blended into the water phase or the oil phase of each recipe for the emulsification. Specifically, the ultraviolet light protection powder is dispersed and mixed in the oil phase containing the quarternary ammonium salt type cation surfactant, the fatty acid or higher alcohol which is liquid at normal temperatures and the oil component, and then the water phase in which the water swelling clay mineral is dispersed and mixed is added to this, followed by mixing and stirring to obtain the target sunscreen cosmetic.

Furthermore, it is also possible to prepare the organic modified clay mineral in advance by treating the water swelling clay mineral with the quarternary ammonium salt type cation surfactant, and then blend the organic modified clay mineral, the fatty acid or higher alcohol which is liquid at normal temperatures, and the ultraviolet light protection powder into the water phase or the oil phase in each recipe for emulsification. Specifically, the organic modified clay mineral, which has been prepared by treating the water swelling clay mineral with the quarternary ammonium salt type cation surfactant, and the ultraviolet light protection powder are dispersed and mixed in the oil phase containing the oil component(s), and then the water phase is added to it, followed by mixing and stirring to obtain the target sunscreen cosmetic.

An ultraviolet light absorbent can be blended into the sunscreen cosmetic of the present invention as necessary. Examples of the ultraviolet light absorbents are: benzoic acid type ultraviolet light absorbents including paraamino benzoic acid (hereafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester and N,N-dimethyl PABA ethyl ester; anthranilic acid type ultraviolet light absorbents including homomentyl-N-acetyl anthranilate; salicylic acid type ultraviolet light absorbents including amyl salicylate, mentyl salicylate, homomentyl salicylate, octyl salicylate, phenyl salicylate, benzyl salicylate and p-isopropanolphenyl salicylate; cinnamic acid type ultraviolet light absorbents including octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glyceryl mono-2-ethylhexanoyl-diparamethoxy cinnamate; benzophenone type ultraviolet light absorbents including 2,4-dihydroxy benzophenone, 2,2'-dihydroxy-4-methoxy benzophenone, 2,2'-dihydroxy-4,4'-dimethoxy benzophenone, 2,2',4,4'-tetrahydroxy benzophenone, 2-hydroxy-4-methoxy benzophenone, 2-hydroxy-4-methoxy-4'-methyl benzophenone, 2-hydroxy-4-methoxy benzophenone-5-sulfonate, 4-phenyl benzophenone, 2-ethylhexyl-4'-phenyl-benzophenone-2-carboxylate, 2-hydroxy-4-n-octoxy benzophenone and 4-hydroxy-3-carboxy benzophenone; as well as 3-(4'-methylbenzylidene)-d,l-camphor, 3-benzylidene-d,l-camphor, urocanic acid, ethyl urocanate, 2-phenyl-5-methyl benzoxazol, 2,2'-hydroxy-5-methylphenyl benzotriazol, 2-(2'-hydroxy-5'-t-octylphenyl) benzotriazol, 2-(2'-hydroxy-5'-methylphenyl benzotriazol, dibenzaladine, dianisoylmethane, 4-methoxy-4'-t-butyldibenzoylmethane and 5-(3,3-dimethyl-2-norbornylidene)-3-pentane-2-one.

Other ingredients normally blended into cosmetics, such as water repellent resin powders and/or resin powders including nylon powder, polymethyl methacrylate, styrene-divinyl benzene copolymer, polyethylene powder, porous vinyl-type polymer, acrylate copolymer and polymethyl-sillsesquioxane; humectants; thickeners; lower alcohols; polyhydric alcohols; mucopolysaccharides; preservatives; antioxidants; sequestering agents; pH adjustment agents; anti-inflammatories; drugs including vitamins, amino acids, and hormones; crude drugs; astringents; pigments; dispersing agents; and perfumes can be blended into the sunscreen cosmetic of the present invention as necessary within the range which does not affect the object of the present invention.

EXAMPLES

The present invention is described further in detail below by referring to examples. The present invention is not limited to these examples. The blend ratios are in weight percent units unless specified otherwise.

Example 1

100 g of BENTON 38 (an organic modified clay mineral from Nationalred Co. in the U.S., prepared by treating 100 g of montmorillonite with 100 mili-equivalents of distearyldimethylammonium chloride) was thoroughly dispersed and mixed, using a labo-homogenizer, in a solution of 10 g isostearic acid in 100 ml ethanol. After removing ethanol with an evaporator, the target gelation agent or the emulsifying agent was obtained by drying. The adsorption of isostearic acid was evaluated by means of X-ray diffraction analysis.

Example 2

100 g of BENTON 38 (an organic modified clay mineral from Nationalred Co. in the U.S., prepared by treating 100 g of montmorillonite with 100 mili-equivalents of distearyldimethylammonium chloride) was thoroughly dispersed and mixed, using a labo-homogenizer, in a solution of 50 g isostearic acid in 100 ml ethanol. After removing ethanol with an evaporator, the target gelation agent or the emulsifying agent was obtained by drying. The adsorption of isostearic acid was evaluated by means of X-ray diffraction analysis.

Example 3

100 g of BENTON 38 (an organic modified clay mineral from Nationalred Co. in the U.S., prepared by treating 100 g of montmorillonite with 100 mili-equivalents of distearyldimethylammonium chloride) was thoroughly dispersed and mixed, using a labo-homogenizer, in a solution of 200 g isostearic acid in 100 ml ethanol. After removing ethanol with an evaporator, the target gelation agent or the emulsifying agent was obtained by drying. The adsorption of isostearic acid was evaluated by means of X-ray diffraction analysis.

For the gelation agents or the emulsifying agents of the present invention obtained in Examples 1–3 and BENTON 38, the organic modified clay mineral, the interlayer spacing values obtained by the X-ray diffraction analysis are shown in Table 1.

TABLE 1

|  | BENTON 38 | Example 1 | Example 2 | Example 3 |
|---|---|---|---|---|
| Interlayer spacing value obtained by X-ray diffraction analysis | 26.5 angstroms | 32.5 angstroms | 40.3 angstroms | 45.0 angstroms |

Table 1 indicates that the interlayer spacing of the organic modified clay mineral (Benton) increases as it is treated with a greater amount of isostearic acid. This increase is believed to be due to the bonding of the fatty acid.

Example 4

The gelation agent or the emulsifying agent was obtained in the same manner as in Example 1 except for the fact that isostearyl alcohol was used instead of isostearic acid.

Example 5

The gelation agent or the emulsifying agent was obtained in the same manner as in Example 2 except for the fact that isostearyl alcohol was used instead of isostearic acid.

Example 6

The gelation agent or the emulsifying agent was obtained in the same manner as in Example 3 except for the fact that isostearyl alcohol was used instead of isostearic acid.

For the gelation agents or the emulsifying agents of the present invention obtained in Examples 4–6 and Benton 38, the organic modified clay mineral, the interlayer spacing values obtained by the X-ray diffraction analysis are shown in Table 2.

TABLE 2

|  | BENTON 38 | Example 1 | Example 2 | Example 3 |
|---|---|---|---|---|
| Interlayer spacing value obtained by X-ray diffraction analysis | 26.5 angstroms | 29.0 angstroms | 39.7 angstroms | 44.1 angstroms |

Table 2 indicates that the interlayer spacing of the organic modified clay mineral (BENTON 38) increases as it is treated with a greater amount of isostearyl alcohol. This increase is believed to be due to the bonding of the higher alcohol.

(1) Examples of the Gel Composition

Example 7

A disper was used to disperse and mix 10 parts of the gelation agent obtained in Example 2 with 90 parts of liquid paraffin to obtain an oil based gel composition.

Example 8

A disper was used to disperse and mix 20 parts of the gelation agent obtained in Example 2 with 80 parts of glyceryl 2-ethylhexanoate to obtain an oil based gel composition.

Example 9

A disper was used to disperse and mix 20 parts of the gelation agent obtained in Example 2 with 10 parts of ethylene glycol dioleate POE (12) dioleate and 70 parts of glyceryl 2-ethylhexanoate to obtain an oil based gel composition.

Comparative Example 1

A disper was used to disperse and mix 10 parts of BENTON 38 with 90 parts of liquid paraffin to obtain an oil based gel composition.

Comparative Example 2

A disper was used to disperse and mix 20 parts of BENTON 38 with 80 parts of glyceryl 2-ethylhexanoate to obtain an oil based gel composition.

Comparative Example 3

A disper was used to disperse and mix 20 parts of BENTON 38 with 10 parts of ethylene glycol dioleate POE (12) dioleate and 70 parts of glyceryl 2-ethylhexanoate to obtain an oil based gel composition.

The oil based gel compositions obtained in Examples 7, 8, and 9 and the oil based gel compositions obtained in Comparative examples 1, 2, and 3 were let stand for two weeks at 50°Å and their stability evaluated using the following evaluation criteria is shown in Table 3. Sensory evaluation of the usability was carried out by a panel of ten specialists using the following evaluation criteria and the results are shown in Table 3.

"Stability Evaluation Criteria"
●: No oil separation is observed.
¤: Oil separation is observed.
X: Extreme oil separation is observed.

"Usability Evaluation Criteria"
●: Eight or more out of ten reported spreadability and usability were good.
○: Six or more and less than eight out of ten reported spreadability and usability were good.
¤: Four or more and less than six out of ten reported spreadability and usability were good.
X: Less than four out of ten reported spreadability and usability were good.

TABLE 3

|  | Ex. 7 | Ex. 8 | Ex. 9 | Comp. Ex. 1 | Comp. Ex. 2 | Comp. Ex. 3 |
|---|---|---|---|---|---|---|
| Stability | ● | ● | ● | ¤ | X | X |
| Usability | ● | ● | ● | ¤ | ○ | ○ |

As clearly shown in Table 3, the gelation agent of the present invention can produce an oil based gel composition with superior temperature stability and usability in both the nonpolar oil system and the polar oil system. On the other hand, a stable oil based gel composition could not be obtained with any of the Comparative examples, and the usability was also inferior compared with that of the Examples.

Other examples of the gel composition prepared by using the gelation agent of the present invention are shown below.

Example 10

Sunscreen

| | |
|---|---|
| BEAGUM (water swelling clay mineral from Vanderbilt Co., U.S.A.) | 2.0 wt % |
| Benzyldimethylstearylammonium chloride | 1.0 |
| Isostearic acid | 1.0 |
| Liquid paraffin | Balance |
| Vaseline | 10.0 |
| Decamethylcyclopentasiloxane | 20.0 |
| Water repellent titanium oxide | 10.0 |
| Octylmethoxycinnamic acid | 5.0 |
| Perfume | Appropriate amount |

(Preparation Method)

BEAGUM was dispersed in ethanol and benzyldimethylstearylammonium chloride was added to this. After raising the temperature up to 50°Å, the mixture was dispersed with a disper. Ethanol was then removed by thorough drying to obtain the organic modified clay mineral. The rest of the ingredients were added to the organic modified clay mineral and kneaded together twice by using a roller with 15 kg/cm pressure to obtain the sunscreen which is the gel composition of the present invention. The obtained sunscreen had good temperature stability, spreadability, and usability.

Example 11
Oil Based Ointment

| | |
|---|---|
| Organic modified clay mineral (BENTON 38) | 5.0 wt % |
| Oleic acid | 5.0 |
| Liquid paraffin | Balance |
| Vaseline | 5.0 |
| Microcrystalline wax | 5.0 |
| Glycerine | 2.0 |
| Drug | Appropriate amount |

(Preparation Method)

Oleic acid, liquid paraffin, vaseline, microcrystalline wax, and glycerine were homogeneously dissolved at 70° C. BENTON 38 was then added to this while stirring with a disper to obtain the oil based ointment which was the gel composition of the present invention. The obtained oil based ointment had good temperature stability, spreadability, and usability.

Example 12
Sunscreen

| | |
|---|---|
| Beagum (water swelling clay mineral from Vanderbilt Co., U.S.A.) | 2.0 wt % |
| Benzyldimethylstearylammonium chloride | 1.0 |
| Isostearyl alcohol | 2.0 |
| Isoparaffin | Balance |
| Vaseline | 10.0 |
| Decamethylcyclopentasiloxane | 20.0 |
| Water repellent titanium oxide | 10.0 |
| Octylmethoxycinnamic acid | 5.0 |
| Perfume | Appropriate amount |

(Preparation Method)

BEAGUM was dispersed in ethanol and benzyldimethylstearylammonium chloride was added to this. After raising the temperature up to 50° C., the mixture was dispersed with a disper. Ethanol was then removed by thorough drying to obtain the organic modified clay mineral. The rest of the ingredients were added to the organic modified clay mineral and kneaded together twice by using a roller with 15 kg/cm pressure to obtain the sunscreen which is the gel composition of the present invention. The obtained sunscreen had good temperature stability, spreadability, and usability.

Example 13
Oil Based Ointment

| | |
|---|---|
| Organic modified clay mineral (BENTON 38) | 5.0 wt % |
| Octyldodecanol | 5.0 |
| Liquid paraffin | Balance |
| Vaseline | 5.0 |
| Microcrystalline wax | 5.0 |
| Glycerine | 2.0 |
| Drug | Appropriate amount |

(Preparation Method)

Octyldodecanol, liquid paraffin, vaseline, microcrystalline wax, and glycerine were homogeneously dissolved at 70° C. BENTON 38 was then added to this while stirring with a disper to obtain the oil based ointment which was the gel composition of the present invention. The obtained oil based ointment had good temperature stability, spreadability, and usability.

(2) Examples of the Emulsified Composition

Example 14

One part of the emulsifying agent obtained in Example 2 and 30 parts of liquid paraffin were dispersed and mixed with a disper, and then 69 parts of purified water was added to this, followed by mixing using the disper to obtain the emulsified composition.

Example 15

Two parts of the emulsifying agent obtained in Example 2 and 20 parts of glyceryl tri-2-ethylhexanoate were dispersed and mixed with a disper, and then 78 parts of purified water was added to this, followed by mixing using the disper to obtain the emulsified composition.

Example 16

Two parts of the emulsifying agent obtained in Example 2 and 20 parts of methylphenylsiloxane were dispersed and mixed with a disper, and then 78 parts of purified water was added to this, followed by mixing using the disper to obtain the emulsified composition.

Comparative Example 4

A disper was used to disperse and mix two parts of BENTON 38 and one part of polyoxyalkylene modified organopolysiloxane with 30 parts of liquid paraffin, and then 67 parts of purified water was added to this, followed by mixing using the disper to obtain the emulsified composition.

Comparative Example 5

A disper was used to disperse and mix two parts of BENTON 38 and one part of glycerol isostearate with 20 parts of methylphenylsiloxane, and then 77 parts of purified water was added to this, followed by mixing using the disper to obtain the emulsified composition.

Comparative Example 6

A disper was used to disperse and mix two parts of BENTON 38 and one part of glycerol isostearate with 20 parts of glyceryl tri-2-ethylhexanoate, and then 77 parts of purified water was added to this, followed by mixing using the disper to obtain the emulsified composition.

Comparative Example 7

A disper was used to disperse and mix two parts of BENTON 38 and five parts of glycerol isostearate with 20 parts of glyceryl tri-2-ethylhexanoate, and then 73 parts of purified water was added to this, followed by mixing using the disper to obtain the emulsified composition.

The emulsified compositions obtained in Examples 14, 15, and 16 and the emulsified compositions obtained in Comparative examples 5, 6, 7, and 8 were let stand for two weeks at 50° C. and their stability evaluated using the following evaluation criteria is shown in Table 4. Sensory evaluation of the usability was carried out by a panel of ten specialists using the following evaluation criteria and the results are shown in Table 4.

"Stability Evaluation Criteria"
●: No oil separation is observed.
¤: Oil separation is observed.
X: Extreme oil separation is observed.
"Usability Evaluation Criteria"
●: Eight or more out of ten reported spreadability and usability were good.
o: Six or more and less than eight out of ten reported spreadability and usability were good.
¤: Four or more and less than six out of ten reported spreadability and usability were good.
X: Less than four out of ten reported spreadability and usability were good.

TABLE 4

|  | Ex. 14 | Ex. 15 | Ex. 16 | Comp. Ex. 4 | Comp. Ex. 5 | Comp. Ex. 6 | Comp. Ex. 7 |
| --- | --- | --- | --- | --- | --- | --- | --- |
| Stability | ● | ● | ● | X | X | ¤ | ● |
| Usability | o | ● | ● | ¤ | o | o | X |

As clearly shown in Table 4, the emulsifying agent composition of the present invention can produce an emulsified composition with superior temperature stability and usability in both the nonpolar oil system and the polar oil system. On the other hand, a stable emulsified composition could not be obtained with Comparative examples 5, 6, or 7. The stable emulsified composition obtained in Comparative example 8 was inferior to those in the Examples in terms of usability.

Other examples of the emulsified composition prepared by using the emulsifying agent of the present invention are shown below.

Example 17
Whitening Cream

| | |
| --- | --- |
| BEAGUM (water swelling clay mineral from Vanderbilt Co. in the U.S.) | 2.0 wt % |
| Benzyldimethylstearylammonium chloride | 1.0 |
| Isostearic acid | 1.0 |
| Decamethylcyclopentasiloxane | 25.0 |
| Ascorbyl glucoside | 1.0 |
| Sodium carboxymethyl cellulose | 1.0 |
| Citric acid | 0.05 |
| Sodium citrate | 0.5 |
| Glycerine | 5.0 |
| 1,3 butylene glycol | 5.0 |
| Methyl parahydroxybonzoate | 0.1 |
| Perfume | 0.05 |
| Purified water | Balance |

(Preparation Method)
BEAGUM was dispersed in ethanol and benzyldimethylstearylammonium chloride was added to this. After raising the temperature up to 50° C., the mixture was dispersed with a disper. Ethanol was then removed by thorough drying to obtain the organic modified clay mineral. Isostearic acid was then added to the organic modified clay mineral, and kneaded together twice using a roller of 15 kg/cm pressure to obtain the emulsifying agent of the present invention. Decamethylcyclopentasiloxane was added to the obtained emulsifying agent to prepare the oil phase, to which the remaining water phase was gradually added while stirring with a disper-homogenizer to obtain the whitening cream.

Example 18
Hand Cream

| | |
| --- | --- |
| Organic modified clay mineral (BENTON 38) | 1.0 wt % |
| Oleic acid | 2.0 |
| Liquid paraffin | 10.0 |
| Squalane | 5.0 |
| Vaseline | 2.0 |
| Microcrystalline wax | 1.0 |
| Cetyl isooctanoate | 5.0 |
| Glycerine | 10.0 |
| Drug | Appropriate amount |
| Ethyl parahydroxybenzoate | 0.1 |
| Perfume | 0.05 |
| Purified water | Balance |

(Preparation Method)
Oleic acid, liquid paraffin, squalane, vaseline, microcrystalline wax, and cetyl octanoate were homogeneously dissolved at 80° C. BENTON 38 was then added to this while stirring with a disper to obtain the oil phase, to which the remaining water phase was gradually added while stirring with a disper-homogenizer to obtain the hand cream. The obtained hand cream had good temperature stability, spreadability, and usability.

Example 19
Sunscreen

| | |
| --- | --- |
| Organic modified clay mineral (BENTON 38) | 2.0 wt % |
| Ethanol | 5.0 |
| Isostearic acid | 2.0 |
| Octylmethoxy cinnamate | 10.0 |
| 4-tert-butyl-4'-methoxydibenzoylmethane | 2.0 |
| Dioctyl succinate | 10.0 |
| Decamethylcyclopentasiloxane | 10.0 |
| Glycerine | 10.0 |
| Drug | Appropriate amount |
| Ethyl parahydroxybenzoate | 0.25 |
| Perfume | 0.05 |
| Purified water | Balance |

(Preparation Method)
BENTON 38 was dispersed in ethanol, isostearic acid was added to this, and the mixture was kneaded together twice by using a roller of 15 kg/cm pressure to obtain the emulsifying agent of the present invention. Octylmethoxy cinnamate, 4-tert-butyl-4'-methoxydibenzoylmethane, dioctyl succinate, and decamethylcyclopentasiloxane were added to the obtained emulsifying agent to obtain the oil phase, to which the remaining water phase was gradually added while stirring with a disper-homogenizer to obtain the sunscreen. The obtained sunscreen had good temperature stability, spreadability, and usability as well as a high sunscreening effect.

Example 20
Whitening Cream

| | |
| --- | --- |
| BEAGUM (water swelling clay mineral from Vanderbilt Co. in the U.S.) | 2.0 wt % |
| Benzyldimethylstearylammonium chloride | 1.0 |
| Isostearyl alcohol | 1.0 |
| Decamethylcyclopentasiloxane | 25.0 |
| Ascorbyl glucoside | 1.0 |
| Sodium carboxymethyl cellulose | 1.0 |

-continued

| | |
|---|---|
| Citric acid | 0.05 |
| Sodium citrate | 0.5 |
| Glycerine | 5.0 |
| 1,3 butylene glycol | 5.0 |
| Methyl parahydroxybonzoate | 0.1 |
| Perfume | 0.05 |
| Purified water | Balance |

(Preparation Method)

BEAGUM was dispersed in ethanol and benzyldimethylstearylammonium chloride was added to this. After raising the temperature up to 50° C., the mixture was dispersed with a disper. Ethanol was then removed by thorough drying to obtain the organic modified clay mineral. Isostearyl alcohol was then added to the organic modified clay mineral and kneaded together twice by using a roller of 15 kg/cm pressure to obtain the emulsifying agent of the present invention. Decamethylcyclopentasiloxane was added to the obtained emulsifying agent to prepare the oil phase, to which the remaining water phase was gradually added while stirring with a disper-homogenizer to obtain the whitening cream.

Example 21

Hand Cream

| | |
|---|---|
| Organic modified clay mineral (BENTON 38) | 1.0 wt % |
| Oleyl alcohol | 2.0 |
| Liquid paraffin | 10.0 |
| Squalane | 5.0 |
| Vaseline | 2.0 |
| Microcrystalline wax | 1.0 |
| Cetyl isooctanoate | 5.0 |
| Glycerine | 10.0 |
| Drug | Appropriate amount |
| Ethyl parahydroxybenzoate | 0.1 |
| Perfume | 10.05 |
| Purified water | Balance |

(Preparation Method)

Oleyl alcohol, liquid paraffin, squalane, vaseline, microcrystalline wax, and cetyl octanoate were homogeneously dissolved at 80° C. BENTON 38 was then added to this while stirring with a disper to obtain the oil phase, to which the remaining water phase was gradually added while stirring with a disper-homogenizer to obtain the hand cream. The obtained hand cream had good temperature stability, spreadability, and usability.

Example 22

Sunscreen

| | |
|---|---|
| Organic modified clay mineral (BENTON 38) | 2.0 wt % |
| Ethanol | 5.0 |
| Octyldodecanol | 1.0 |
| Octylmethoxy cinnamate | 10.0 |
| 4-tert-butyl-4'-methoxydibenzoylmethane | 2.0 |
| Dioctyl succinate | 10.0 |
| Decamethylcyclopentasiloxane | 10.0 |
| Glycerine | 10.0 |
| Drug | Appropriate amount |
| Ethyl parahydroxybenzoate | 0.25 |
| Perfume | 0.05 |
| Purified water | Balance |

(Preparation Method)

BENTON 38 was dispersed in ethanol, octyldodecanol was added to this, and the mixture was kneaded together twice by using a roller of 15 kg/cm pressure to obtain the emulsifying agent of the present invention. Octylmethoxy cinnamate, 4-tert-butyl-4'-methoxydibenzoylmethane, dioctyl succinate, and decamethylcyclopentasiloxane were added to the obtained emulsifying agent to obtain the oil phase, to which the remaining water phase was gradually added while stirring with a disper-homogenizer to obtain the sunscreen. The obtained sunscreen had good temperature stability, spreadability, and usability as well as a high sunscreening effect.

(3) Examples of the Sunscreen Cosmetic

Example 23

Sunscreen Cream

| | |
|---|---|
| (1) Decamethylcyclopentasiloxane | 25.0 wt % |
| (2) Liquid paraffin | 5.0 |
| (3) Isostearic acid | 1.0 |
| (4) Distearyldimethylammonium chloride | 0.6 |
| (5) Octylmethoxy cinnamate | 5.0 |
| (6) Paraben | Appropriate amount |
| (7) Perfume | Appropriate amount |
| (8) Water repellent spindle-shaped titanium oxide | 10.0 |
| (9) Ion exchanged water | Balance |
| (10) Glycerine | 10.0 |

(Preparation Method)

(1)–(7) were heated up to 70° C. to prepare the oil phase in advance. (8) was then added to this and dispersed and mixed with a disper. (9)–(11) were dispersed and mixed at 70° C., gradually added to the oil phase while stirring, thoroughly homogeneously mixed and stirred, and cooled to obtain the target sunscreen cream.

Comparative Example 8

Sunscreen Cream

A sunscreen cream was prepared in the same manner as in Example 23 except for the fact that polyoxyalkylene modified organopolysiloxane was used instead of isostearic acid.

Example 24

Sunscreen Cream

| | |
|---|---|
| (1) Decamethylcyclopentasiloxane | 20.0 wt % |
| (2) Liquid paraffin | 10.0 |
| (3) Decyltetradecanol | 2.0 |
| (4) Distearyldimethylammonium chloride | 0.6 |
| (5) Octylmethoxy cinnamate | 5.0 |
| (6) Ethanol | 2.0 |
| (7) Paraben | Appropriate amount |
| (8) Perfume | Appropriate amount |
| (9) Water repellent spindle-shaped titanium oxide | 5.0 |
| (10) Water repellent zinc oxide | 5.0 |
| (11) Ion exchanged water | Balance |
| (12) Glycerine | 5.0 |
| (13) Smectone | 1.0 |

(Preparation Method)

(1)–(8) were heated up to 70° C. to prepare the oil phase in advance. (9) and (10) were then added to this and dispersed and mixed with a disper. (11)–(13) were dispersed and mixed at 70° C., gradually added to the oil phase while stirring, thoroughly homogeneously mixed and stirred, and cooled to obtain the target sunscreen cream.

Example 25
Cream-Type Foundation

| | |
|---|---|
| (1) Decamethylcyclopentasiloxane | 30.0 wt % |
| (2) Liquid paraffin | 10.0 |
| (3) Oleic acid | 0.1 |
| (4) Distearyldimethylammonium chloride | 0.05 |
| (5) Octylmethoxy cinnamate | 8.0 |
| (6) Paraben | Appropriate amount |
| (7) Perfume | Appropriate amount |
| (8) Water repellent titanium oxide | 5.0 |
| (9) Water repellent zinc oxide | 5.0 |
| (10) Talc | 20.0 |
| (11) Colored pigment | Appropriate amount |
| (12) Ion exchanged water | Balance |
| (13) Glycerine | 5.0 |
| (14) Smectone | 0.2 |

(Preparation Method)

(1)–(7) were heated up to 70° C. to prepare the oil phase in advance. (8)–(11) were then added to this and dispersed and mixed with a disper. (12)–(14) were dispersed and mixed at 70° C., gradually added to the oil phase while stirring, thoroughly homogeneously mixed and stirred, and cooled to obtain the target cream type foundation.

Example 26
Sunscreen Cream

| | |
|---|---|
| (1) Liquid paraffin | 20.0 wt % |
| (2) Glyceryl trioctanoate | 5.0 |
| (3) Isostearic acid | 2.0 |
| (4) Distearyldimethylammonium chloride | 0.05 |
| (5) Octylmethoxy cinnamate | 5.0 |
| (6) 2-hydroxy-4-methoxybenzophenone | 2.0 |
| (7) Paraben | Appropriate amount |
| (8) Perfume | Appropriate amount |
| (9) Water repellent titanium oxide | 1.0 |
| (10) Ion exchanged water | Balance |
| (11) 1,3 butylene glycol | 5.0 |
| (12) Beagum | 0.5 |

(Preparation Method)

(1)–(8) were heated up to 70° C. to prepare the oil phase in advance. (9) was then added to this and dispersed and mixed with a disper. (10)–(12) were dispersed and mixed at 70° C., gradually added to the oil phase while stirring, thoroughly homogeneously mixed and stirred, and cooled to obtain the target sunscreen cream.

Example 27
Sunscreen Cream

| | |
|---|---|
| (1) Decamethylcyclopentasiloxane | 28.0 wt % |
| (2) Isostearyl alcohol | 5.0 |
| (3) Octylmethoxy cinnamate | 10.0 |
| (4) 2-hydroxy-4-methoxybenzophenone | 0.5 |
| (5) Paraben | Appropriate amount |
| (6) Perfume | Appropriate amount |
| (7) BENTON 38 | 2.0 |
| (8) Water repellent spindle-shaped titanium oxide | 20.0 |
| (9) Water repellent zinc oxide | 3.0 |
| (10) Polymethyl sesquioxane | 5.0 |
| (11) Ion exchanged water | Balance |
| (12) 1,3 butylene glycol | 5.0 |

(Preparation Method)

(1)–(6) were heated up to 70° C. to prepare the oil phase in advance. (7)–(9) were then added to this and dispersed and mixed with a disper. (10)–(12) were dispersed and mixed at 70° C., gradually added to the oil phase while stirring, thoroughly homogeneously mixed and stirred, and cooled to obtain the target sunscreen cream. For the water repellent spindle-shaped titanium oxide, the fine particle titanium oxide 100-T (Teikoku Kako Co.) was used. BENTON 38 is an organic modified clay mineral prepared by treating 100 g of montmorillonite with 100 mili-equivalents of distearyldimethylammonium chloride (from Nationalred Co., U.S.A.).

Comparative Example 9
Sunscreen Cream

A sunscreen cream was prepared in the same manner as in Example 27 except for the fact that polyoxyalkylene modified organopolysiloxane was used instead of isostearic acid and water repellent titanium oxide with an average particle size of 0.03–0.04 micrometers and an average diameter/minor axis ratio of 1.3 was used instead of the water repellent spindle-shaped titanium oxide.

For the sunscreen cosmetics obtained as mentioned above, the following test of the degree of the inconspicuousness of the whiteness was carried out. The results are shown in Table 5.

(1) Testing for the Conspicuousness of the Whiteness

For a panel of 20 evaluation specialists, the sample (Examples 1–5 and Comparative examples 1–2) was applied on the medial aspect of the forearm. After waiting for 30 minutes, the conspicuousness of the whiteness was evaluated.

(2) Testing for the Conspicuousness of the Whiteness After Water Rinsing

After evaluating the conspicuousness of the whiteness with method (1), the applied site was rinsed with running water (30° C.) for 10 minutes and then the conspicuousness of the whiteness was evaluated.

The test results of (1) and (2) were obtained based on the following evaluation criteria.

(Evaluation Criteria)

16 or more out of 20 reported the whiteness was not conspicuous:
●

12 or more out of 20 reported the whiteness was not conspicuous:
○

6 or more out of 20 reported the whiteness was not conspicuous:
¤

Less than 6 out of 20 reported the whiteness was not conspicuous:
X

TABLE 5

|  | Ex. 23 | Ex. 24 | Ex. 25 | Ex. 26 | Ex. 27 | Comp. Ex. 8 | Comp. Ex. 9 |
| --- | --- | --- | --- | --- | --- | --- | --- |
| Testing for the conspicuosness of the whiteness | ○ | ○ | ○ | ● | ● | ○ | ¤ |
| Testing for the conspicuousness of the whiteness after water rinsing | ○ | ○ | ○ | ● | ● | X | X |

As clearly shown in Table 5, Examples of the present invention are superior sunscreen cosmetics with which the whiteness after water rinsing is not conspicuous.

INDUSTRIAL APPLICABILITY OF THE INVENTION

As described thus far, the present invention can provide a gelation agent or an emulsifying agent which can be added and mixed to a wide range of oils to produce an oil based gel composition or an emulsified composition with superior stability, safety and usability, as well as a gel composition or an emulsified composition which uses this agent.

The gelation agent or the emulsifying agent of the present invention or the gel composition or the emulsified composition using this agent is preferably used as the base agent of cosmetics and quasi-drugs, for example.

Also, the present invention can provide a sunscreen cosmetic with superior usability, i.e. it exhibits good adhesion to the skin and superior water resistance and it does not become conspicuous when the applied site comes in contact with sweat or water from the ocean or pool. The present invention is particularly useful when a high ultraviolet light protection effect is desired because it allows the required amount of the ultraviolet light protection powder to be blended in without concern for conspicuous whiteness. ter.

What is claimed is:

1. A gelation agent obtained by mixing a water swelling clay mineral with a quaternary ammonium salt cation surfactant, said water swelling clay mineral comprising a colloidal hydrated aluminum silicate with a three-layer structure represented by the following formula:

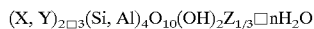

$(X, Y)_{2\square3}(Si, Al)_4O_{10}(OH)_2Z_{1/3}\square nH_2O$ wherein
X is Al, Fe(III), Mn(III), or Cr(III);
Y is Mg, Fe(II), Ni, Zn, Li, or Mn(II);
Z is K, Na, 1/2Ca, or 1/2Mg; and
n is a natural number greater than 0;
and said quaternary ammonium salt cation surfactant is represented by the following formula:

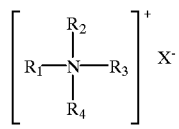

where $R_1$ denotes a benzyl group or alkyl group with a carbon number of 10–22, $R_2$ denotes a methyl group or alkyl group with a carbon number of 10–22, $R_3$ and $R_4$ are hydroalkyl groups or alkyl groups with a carbon number of 1–3, and X denotes a halogen atom or methyl sulfate residue, and a fatty acid which is liquid at normal temperatures,
said quaternary ammonium salt cation surfactant being present in an amount of 60–140 milli-equivalents for 100 g of said water swelling clay, and said fatty acid being present in an amount of 1–300 g for 100 g of water swelling clay mineral.

2. A gel composition comprising the gelation agent of claim 1, and an oil component.

3. A gelation agent obtained by mixing a water swelling clay mineral with a quaternary ammonium salt cation surfactant, said water swelling clay mineral comprising a Colloidal hydrated aluminum silicate with a three-layer structure represented by the following formula:

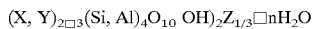

$(X, Y)_{2\square3}(Si, Al)_4O_{10}\ OH)_2Z_{1/3}\square nH_2O$ wherein
X is Al, Fe(III), Mn(III), or Cr(III);
Y is Mg, Fe(II), Ni, Zn, Li, or Mn(II);
Z is K, Na, 1/2Ca, or 1/2Mg; and
n is a natural number greater than 0;
and said guaternary ammonium salt cation surfactant is represented by the following formula:

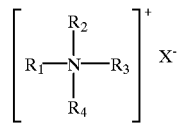

where $R_1$ denotes a benzyl group or alkyl group with a carbon number of 10–22; $R_2$ denotes a methyl group or alkyl group with a carbon number of 10–22, $R_3$ and $R_4$ are hydroalkyl groups or alkyl groups with a carbon number of 1–3, and X denotes a halogen atom or methyl sulfate residue, and a higher alcohol which is liquid at normal temperatures,
said quaternary ammonium salt cation surfactant being present in an amount of 60–140 mili-equivalents for 100 g of said water swelling clay, and said higher alcohol being present in an amount of 1–500 g for 100 g of water swelling clay mineral.

4. A gel composition comprising the gelation agent of claim 3, and an oil component.

5. An emulsified composition comprising the gellation agent of claim 1, an oil component and water.

6. A sunscreen cosmetic which is the emulsified composition of claim 2, additionally containing ultraviolet light protection powder.

7. An emulsified composition comprising the gelation agent of claim 3, an oil component and water.

8. A sunscreen cosmetic which is the emulsified composition of claim 7, additionally containing ultraviolet light protection powder.

9. A gelation agent obtained by mixing a water swelling clay mineral with a guaternary ammonium salt cation surfactant, said water swelling clay mineral comprising a colloidal hydrated aluminum silicate with a three-layer structure represented by the following formula:

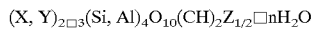

wherein
- A is Al, Fe(III), Mn(III), or Cr(III);
- Y is Mg, Fe(III), Ni, Zn, Li, or Mn(II);
- 2 is X, Na, 1/2Ca, or 1/2Mg; and
- n is a natural number greater than 0;

and said quaternary ammonium salt cation surfactant is represented by the following formula:

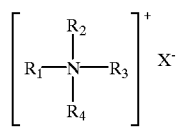

where $R_1$ denotes a benzyl group or alkyl group with a carbon number of 10–22, $R_2$ denotes a methyl group or alkyl group with a carbon number of 10–22, $R_3$ and $R_4$ are hydroalkyl groups or alkyl groups with a carbon number of 1–3, and X denotes a halogen atom or methyl sulfate residue; and either a fatty acid or a higher alcohol which is liquid at normal temperatures, said guaternary ammonium salt cation surfactant being present in an amount of 60–140 mili-equivalents for 100 g of sail water swelling clay, and said higher alcohol being present in an amount of 1–500 g for 100 g of water swelling clay mineral, said fatty acid being selected from the group consisting of oleic acid, isostearic acid, linoleic acid, linolenic acid, eicosapentaenoic acid, and docohexaenoic acid, and said higher alcohol being selected from The group consisting of oleyl alcohol, isostearyl alcohol, octyldodecanol, decyltetradecanol, and jojoba alcohol.

10. The gelation agent of claim 1, wherein said fatty acid which is liquid at normal temperature is selected from the group consisting of one or more of oleic acid, isostearic acid, linoleic acid, linolenic acid, eicosapentanoic acid and docohexaneoic acid.

11. The gelation agent of claim 1, wherein said higher alcohol which is liquid at normal temperatures is selected from the group consisting of one or more of oleyl alcohol, isostearyl alcohol, octydodecanol, decyltetradecanol and jojoba alcohol.

* * * * *